United States Patent [19]

Futch, Jr.

[11] Patent Number: 5,511,977

[45] Date of Patent: Apr. 30, 1996

[54] METHOD FOR CONVERTING DENTAL HANDPIECES TO QUICK DISCONNECT

[76] Inventor: Walter B. Futch, Jr., 9322 Sue Cir., Leland, N.C. 28451

[21] Appl. No.: 328,014

[22] Filed: Oct. 24, 1994

[51] Int. Cl.[6] ........................................... A61C 9/00
[52] U.S. Cl. ........................................................ 433/126
[58] Field of Search ........................................... 433/126

[56] References Cited

U.S. PATENT DOCUMENTS

| | | | |
|---|---|---|---|
| 4,477,109 | 10/1984 | Kleuver | 285/361 |
| 4,477,253 | 10/1984 | Euvrard | 433/126 |
| 5,033,960 | 7/1991 | Heil | 433/126 |
| 5,039,304 | 8/1991 | Heil | 433/126 |
| 5,057,015 | 10/1991 | Fleer | 433/126 |
| 5,219,285 | 6/1993 | Meller et al. | 433/126 |

*Primary Examiner*—John J. Wilson
*Attorney, Agent, or Firm*—John G. Mills and Associates

[57] ABSTRACT

This invention is a quick connecting and disconnecting assembly for standard dental handpieces that are normally connected to a supply line by base nut sleeves that are screwed onto the threaded end of such handpieces. This is accomplished by simply replacing the interiorly threaded base nut on the supply line with a base locking sleeve having j-shaped slots in the outer end thereof and telescoping this over an interiorly threaded connector sleeve with exterior lugs thereon mounted on the threaded end of the handpiece so that the lugs can engage the j-shaped slots.

3 Claims, 2 Drawing Sheets

METHOD FOR CONVERTING DENTAL HANDPIECES TO QUICK DISCONNECT

FIELD OF INVENTION

This invention relates to dentistry and more particularly to the connection between dental handpiece and supply lines.

1. Background of the Invention

Dental handpieces used in most dental offices have a head portion on one end and are threaded on the opposite end. A multi-lumen or multi-tube standard line mates with openings in the threaded end of the handpiece and a collar-like, interiorly threaded base nut is used to hold the supply line and the handpiece together.

With the advent of acquired immune deficiency syndrome or AIDS as well as hepatitis and other highly communicable diseases that are transferred by coming into contact with saliva and blood, stringent sterilization procedures are now required. These procedures include changing of the dental handpiece with a sterilized handpiece after each patient use.

The screwing and unscrewing of the interiorly threaded base nut on and off of the threaded end of the hand piece is not only time consuming and labor intensive, but it also eventually causes excessive wear on the threads and premature failure of the supply line to handpiece connection. Further, there is a great chance of contamination of the sterilized handpiece during the laborious screwing and unscrewing of the supply line base nut thereonto.

A number of attempts have been made to construct quick connect and disconnect means for coupling dental handpieces to supply lines. These generally are elaborate mechanisms that require modifications to the handpiece and or supply line or even require new handpieces to fit the quick disconnect coupling. This can of course be very expensive considering the number of patients the average dentist sees each day with each patient requiring his or her own sterilized handpiece.

None of the prior known quick connect and disconnect assemblies for dental handpieces have been designed specifically to convert preexisting dental handpieces from a screw type coupling to a quick connect and disconnect coupling.

2. Concise Explanation of Prior Art

U.S. Pat. No. 5,039,304 to Donald J. Heil, assigned to Midwest Dental Products Corporation of Des Plaines, Ill. is considered of interest in that it discloses a connect/disconnect coupling for dental handpieces that is very complicated and requires springs, special garments, and retainers.

U.S. Pat. No. 3,955,284 to John E. Balson is considered of interest in that it discloses a disposable dental drill assembly that is internally connected to the handle portion of the dental handpiece. This device does not meet the present sterilization requirements where the whole handpiece must be replaced for each patient. Also, this assembly could not be adapted for use with pre-existing dental pieces.

U.S. Pat. No. 4,303,392 to Russell L. Rollofson, assigned to A-Dec, Inc., of Newberg, Oreg. discloses a dental handpiece with quick disconnect coupling similar to a quick disconnect water hose coupling. This system is complex and expensive to make and would be relatively difficult to use.

U.S. Pat. No. 5,219,285 to Moshe Meller, et al, assigned to MTI Precision Products, Inc., of Lakewood, N.J. discloses a disposable right angle dental handpiece that includes a J-shaped slot for quick disconnect. Again this disclosure would have to be specially made for both the handpiece and the supply line coupling which is complicated and would be relatively expensive to the purchasing dentist.

U.S. Pat. No. 5,057,015 to Otto Fleer, assigned to Siemens Aktiengesellschaft, of Munich, Fed. Rep. of Germany discloses a dental handpiece having an arrangement to form compatible connections to differently design rotatable joints. This device is extremely complicated and would be very expensive to produce and could not be adapted to pre-existing handpieces.

U.S. Pat. No. 5,033,960 to Donald J. Heil, assigned to Midwest Dental Products Corporation of Des Plaines, Ill. discloses a dental handpiece connector assembly with replaceable air cooled lamp and insertion/extraction tool therefore and in FIG. 1 discloses a mating coupling with j-shaped slot. This invention however could not be used in retrofitting presently existing dental handpieces and in fact is specifically limited to replaceable air cooled lamps.

U.S. Pat. No. 4,553,938 to Robert A. Olsen, assigned to Sybron Corporation of Rochester, N.Y. discloses a low torsional resistant instrument handpiece hose with an internally threaded supply line base nut that threads onto the external threads of a dental handpiece similar to the prior art herein above described.

U.S. Pat. No. 4,477,253 to Herbert Envrard, assigned to Micro-Mega S. A., of Besancon, France is considered of interest in that it discloses a device for quick coupling of dental appliances in a manner similar to the quick connect/disconnect of water hoses.

Finally, U.S. Pat. Nos. 4,477,109 to Guenther F. Kleuver, assigned to GFK Partnership of Rockford, Ill. and 4,017,103 to Johnathan L. Lorkowski, part interest assigned to The Raymond Lee Organization, Inc. of New York, N.Y. both disclose connectors or couplings for garden hoses.

BRIEF DESCRIPTION OF INVENTION

After much research and study into the above mentioned problems, the present invention has been developed to provide a simple, inexpensive, and yet highly efficient means for converting standard pre-existing dental handpieces with screw connectors between such handpieces and their supply lines to a quick connect disconnect handpiece.

The above is accomplished by simply replacing the interiorly threaded base nut on the supply line with a base locking sleeve having j-shaped slots in the outer end thereof and telescoping this over an interiorly threaded connector sleeve having exterior lugs thereon to engage the j-shaped slots.

The above provides an simple and inexpensive coupling to convert a standard thread connected supply line to dental handpiece to a quick connect disconnect coupling without complicated springs, grommets, rings and the like.

In view of the above it is an object of the present invention to provide a quick disconnect base assembly for pre-existing dental handpieces.

Another object of the present invention is to provide a quick disconnect assembly for dental handpieces that requires no modification to the pre-existing supply line and handpiece.

Another object of the present invention is to provide a quick disconnect assembly that replaces the internally threaded supply line base nut sleeve with a sleeve that has j-shaped slots in the end thereof for engaging a connector sleeve that is internally threaded to a standard, pre-existing dental handpiece and has outwardly projecting lugs for engaging the j-shaped slots of the base nut replacement.

Another object of the present invention is to provide a method of converting thread connected dental handpieces and their respective supply lines to a quick disconnect dental handpiece and supply line.

Other objects and advantages of the present invention will become apparent and obvious from a study of the following description and the accompanying drawings which are merely illustrative of such invention.

DETAILED DESCRIPTION OF INVENTION

Figure 1:
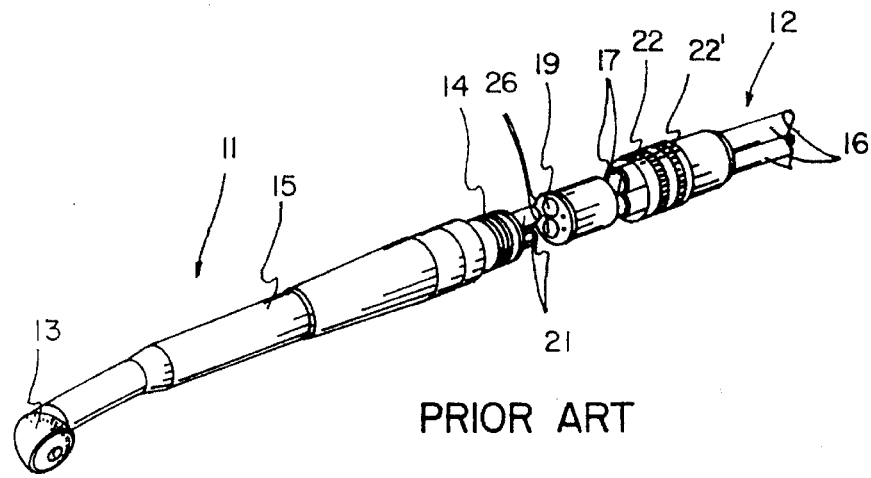
FIG. 1 is an exploded view of the prior art screw coupling between the supply line and the dental handpiece.

With further reference to the drawings, the quick connect and disconnect means of the present invention, indicated generally at 10, is adapting to be used with standard conventional dental handpieces, indicated generally at 11, and their associated supply lines, indicated generally at 12.

The handpiece 11 includes a standard head portion 13 on one end and a threaded connective portion 14 on the opposite end with a handle or grip portion 15 therebetween.

The supply line 12 includes a plurality of tubes 16 of thermoplastic or other suitable material that are usually bonded together. The ends of each of these tubes are adapted to receive hollow studs 17 outwardly projecting from one end of a standard connector 18. A shoulder 19 is provided on the end of connector 18 opposite hollow studs 17. Openings 20 in the shoulder end 19 of connector 18 communicate with the hollow studs 17 and then to the tubes 16.

The end of the threaded connector portion 14 of handpiece 11 has a plurality of outwardly projecting hollow studs 21 which are adapted to be matingly received by end openings 20 of the shoulder end 19 of connector 18.

All of the above described parts of the present invention are standard, pre-existing parts used today in a majority of dental offices and are not in any way modified when used in conjunction with the quick disconnect means 10 of the present invention.

In the prior art described above, a base nut sleeve 22 slides over tubes 16 of the supply line 12 and connector 18 until constriction 22' contacts shoulder 19 of such connector to prevent further longitudent movement. The outer end of the base nut sleeve 22 is interiorly threaded and adapted to matingly thread onto the exterior threads of connector portion 14 of handpiece 11. As the base nut sleeve 22 is screwed down on the threaded connector portion 14 of the handpiece, such handpiece 11 and the supply line 12 will be held tightly in place with the hollow studs 21 of the handpiece matingly inserted into their respective openings 20 of the supply line connector 18 (see prior art FIGS. 1 and 2).

The quick disconnect means of the present invention includes an interiorly threaded connector sleeve 23 and a replacement base locking sleeve 24.

The connector sleeve 23 is adapted to be screwed onto the threaded end 14 of handpiece 11. A pair of outwardly projecting locking pins 25 are provided on opposite sides of connector sleeve 23.

The replacement base locking sleeve 24 has a constriction 24' which, when sleeve 24 is moved longitudinally toward the connector end of the supply line 12, such constriction will contact shoulder 19 and prevent further longitudinal movement of said locking sleeve 24.

A pair of j-shaped slots 26 are provided in the end of replacement base locking sleeve 24.

Figure 2:
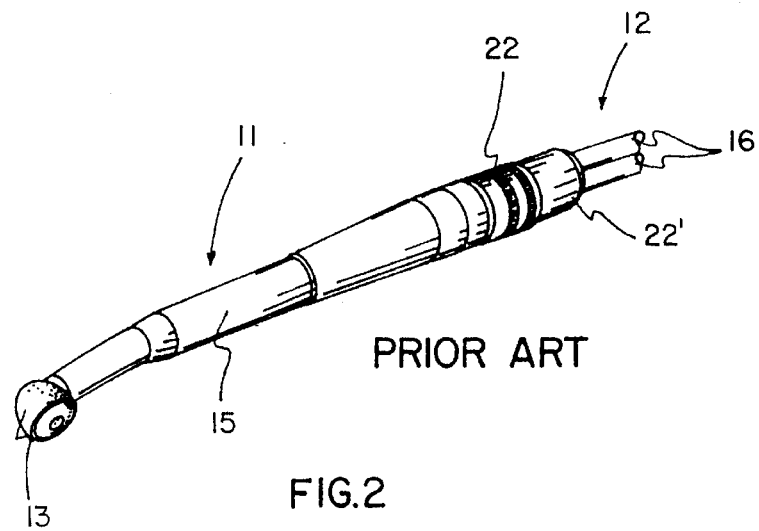
FIG. 2 is an elevation view of the prior art supply line screw coupled with the dental handpiece.

There are a plurality of pre-existing handpieces that are used in dental offices every day that have base nut sleeves on supply lines that screw onto the threaded end of handpiece 11 as shown clearly in prior art FIGS. 1 and 2. These are known in the industry as Mid-West Style Handpieces, Borden Style Handpieces, Safco Style Swivel Adaptors, and Fiber Optic Handpieces. The connector sleeves 23 and the replacement base locking sleeves 24 would of course be sized to fit each of these various standard handpieces and their associated supply lines.

To convert a standard screw connected dental handpiece 11 and supply line 12, the base nut sleeve 21 on the supply line is screwed off of the threaded end of the dental handpiece 11. The tubes 16 are pulled off of the hollow studs 17 of connector 18 and the base nut sleeve 22 removed from the bundle of tubes 16.

Figure 3:
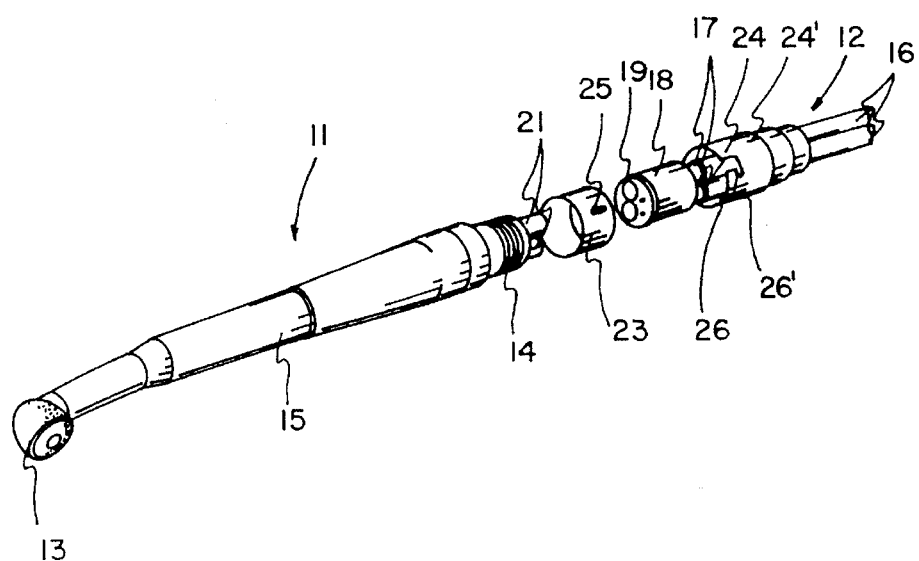
FIG. 3 is an exploded view showing the replacement base locking sleeve on the supply line with the connector sleeve for the dental handpiece.
Figure 4:
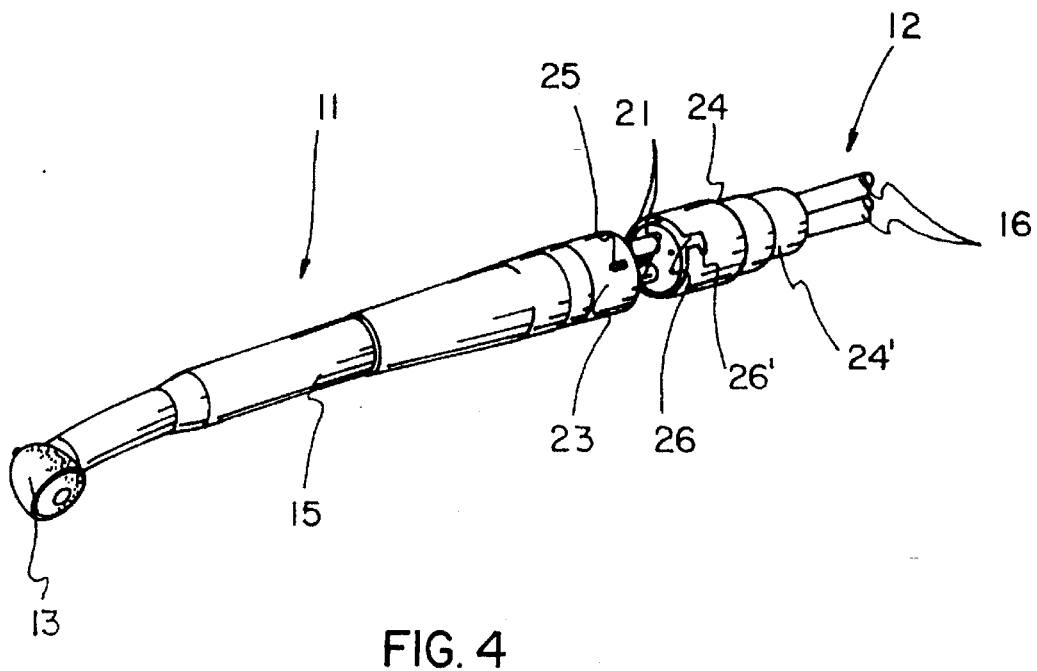
FIG. 4 is an elevation view of the quick disconnect assembly ready for connection.
Figure 5:
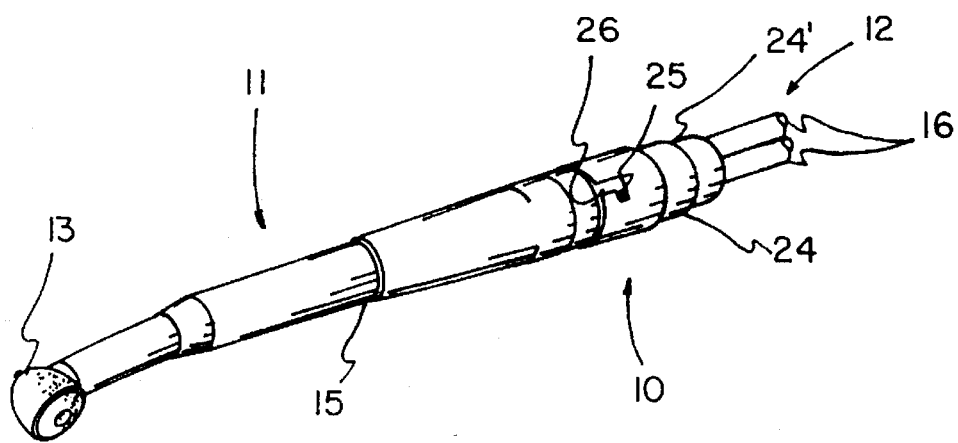
FIG. 5 is an elevation view of the quick disconnect assembly of the present invention with the supply line operatively connected to the dental handpiece.

The base nut sleeve 22 is replaced with base locking sleeve 24 with the bundle of tubes 16 passed longitudinally therethrough and the hollow studs 17 again connected to said tubes 16 as shown in FIG. 3. The internally threaded connector sleeve 23 is then screwed onto the threaded connector portion 14 of handpiece 11 as shown in FIG. 4. The locking pins 25 on connector sleeve 23 are lined up with the j-shaped slots 26 in the end of the replacement base locking sleeve 24. When the end of such locking sleeve is telescopically moved over the connector sleeve 23 and twisted, said locking pins 25 will engage the j-shaped slots 26 to hold the dental handpiece 11 and the supply line 12 firmly in place.

By screwing the connector sleeve 23 inwardly or outwardly on the threaded portion 14 of handpiece 11, the connection between the supply line and the handpiece can be tensioned.

To disconnect the locking sleeve 24 of the quick connect and disconnect means 10 of the present invention, slight longitudinal pressure of sleeve 24 toward handpiece 11 will allow the locking pins 25 of sleeve 23 to twist out of the curved tip 26' of the j-shaped slot 26. The supply line 12 and its associated parts can then be simply moved longitudinally away from the handpiece 11 to disengage the hollow studs 21 from openings 20 so that the handpiece can be removed.

A sterile handpiece 11 can then be quickly connected to the supply line 12 as herein above described.

From the above it can be seen that the present invention has the advantage of providing a means for quick connecting and disconnecting of standard dental handpieces to standard supply lines that ordinarily are connected by threading the base nut sleeve onto the threaded end of the handpiece. By simply removing the base nut sleeve 22 and substituting for the same the replacement base locking sleeve 24 and screwing the connector sleeve 23 onto threads 14 of handpiece 11, the conversion from a labor intensive to a quick connect and disconnect means is accomplished.

The present invention may, of course, be carried out in other specific ways than those herein set forth without departing from the spirit and essential characteristics of such invention. The present embodiments are, therefore, to be considered in all respects as illustrative and not restrictive, and all changes coming within the meaning and equivalency range of the appended claims are intended to be embraced therein.

What is claimed is:

1. A method of converting a pre-existing dental handpiece to a quick connect and disconnect dental handpiece by the installation of quick connect and disconnect means, said pre-existing dental handpiece having a threaded end portion adapted to receive a threaded nut sleeve, said sleeve engaging a connector attached to the end of a supply line, said method comprising: removing said base nut sleeve from said threaded portion of said handpiece and separating said connector therefrom; screwing a connector sleeve having at least one outwardly projecting locking pin on the exterior thereof onto said threaded end portion of said handpiece; removing said base nut sleeve from said supply line and said connector and replacing the same with a base locking sleeve having at least one j-shaped slot in the end thereof; sliding said base locking sleeve over said connector sleeve; and twisting said base locking sleeve to engage said at least one locking pin in said at least one j-shaped slot whereby said pre-existing dental handpiece that is threadably connected to said supply line is converted to a quick connect and disconnect handpiece.

2. The method of claim 1 wherein at least two locking pins are provided on opposite sides of the exterior of said connector sleeve and at least two j-shaped slots are provided on opposite sides of the end of said base locking sleeve.

3. The method of claim 2 wherein said quick connect and disconnect means includes adjustment means in order to vary the tensions on the connection between said supply line and said handpiece.

* * * * *